(12) United States Patent
Newkirk et al.

(10) Patent No.: US 7,083,150 B2
(45) Date of Patent: Aug. 1, 2006

(54) PATIENT LINE MANAGEMENT SYSTEM

(75) Inventors: David C. Newkirk, Lawrenceburg, IN (US); Steven J. Schwartz, Cincinnati, OH (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 10/802,288

(22) Filed: Mar. 17, 2004

(65) Prior Publication Data

US 2004/0232286 A1    Nov. 25, 2004

Related U.S. Application Data

(60) Provisional application No. 60/455,621, filed on Mar. 18, 2003.

(51) Int. Cl.
*F16L 3/00* (2006.01)

(52) U.S. Cl. .......................................... 248/49; 604/151

(58) Field of Classification Search .................. 248/49, 248/74.1, 74.2, 74.3, 75, 51, 52, 61; 604/151
See application file for complete search history.

(56) References Cited

U.S. PATENT DOCUMENTS

| | | | |
|---|---|---|---|
| 3,088,178 A | | 5/1963 | Propst |
| 3,095,625 A | | 7/1963 | Propst |
| 3,675,275 A | * | 7/1972 | Arblaster ..................... 248/75 |
| 3,882,886 A | * | 5/1975 | Ely et al. ..................... 137/899 |
| 4,094,484 A | | 6/1978 | Galione |
| 4,523,683 A | | 6/1985 | Fullenkamp et al. |
| 4,574,963 A | | 3/1986 | Fullenkamp et al. |
| 4,625,936 A | * | 12/1986 | Hadden, Sr. ................. 248/544 |
| 4,632,591 A | | 12/1986 | Fullenkamp |
| 4,662,524 A | | 5/1987 | Fullenkamp et al. |
| 4,738,369 A | | 4/1988 | Desjardins |
| 4,807,659 A | | 2/1989 | Schindele |
| 4,945,592 A | | 8/1990 | Sims et al. |
| 4,993,683 A | | 2/1991 | Kreuzer |
| 5,226,456 A | * | 7/1993 | Semak ........................ 138/107 |
| 5,306,109 A | | 4/1994 | Kreuzer et al. |
| 5,394,592 A | * | 3/1995 | Quick .......................... 24/16 R |
| 5,421,548 A | | 6/1995 | Bennett et al. |
| 5,527,289 A | | 6/1996 | Foster et al. |
| 5,618,090 A | | 4/1997 | Montague et al. |
| 5,677,513 A | * | 10/1997 | Ito et al. .................... 174/72 A |
| 5,678,609 A | * | 10/1997 | Washburn ................... 138/107 |
| 5,878,536 A | | 3/1999 | Demmitt et al. |
| 5,961,193 A | | 10/1999 | Hobbs |
| 6,155,743 A | | 12/2000 | Chen |
| 6,170,102 B1 | | 1/2001 | Kreuzer |
| 6,179,260 B1 | | 1/2001 | Ohanian |
| 6,854,694 B1 | * | 2/2005 | Van Etten ..................... 248/75 |
| 2003/0014817 A1 | | 1/2003 | Gallant et al. |
| 2004/0056155 A1 | * | 3/2004 | Chen et al. .................... 248/49 |

FOREIGN PATENT DOCUMENTS

| | | | | |
|---|---|---|---|---|
| DE | 3814518 | * | 7/1989 | .................. 248/49 |
| DE | 92 04 321.6 | | 5/1992 | |
| EP | 0 215 212 A | | 3/1987 | |

(Continued)

*Primary Examiner*—Ramon O Ramirez
(74) *Attorney, Agent, or Firm*—Barnes & Thornburg LLP

(57) ABSTRACT

A line management system for supporting patient care lines that extend between a patient and patient care equipment is provided. The system has an elongated support member that can be manipulated into a plurality of positions by a caregiver. A line holder is coupled to the support member and is configured to selectively retain lines (tubes).

21 Claims, 2 Drawing Sheets

FOREIGN PATENT DOCUMENTS

| | | |
|---|---|---|
| EP | 0 257 299 A | 3/1988 |
| EP | 0 943 306 B1 | 9/1999 |
| EP | 1 243 900 A2 | 9/2002 |
| FR | 1292174 A | 3/1987 |
| GB | 1 061 383 | 3/1967 |
| WO | WO 00/09061 | 2/2000 |

* cited by examiner

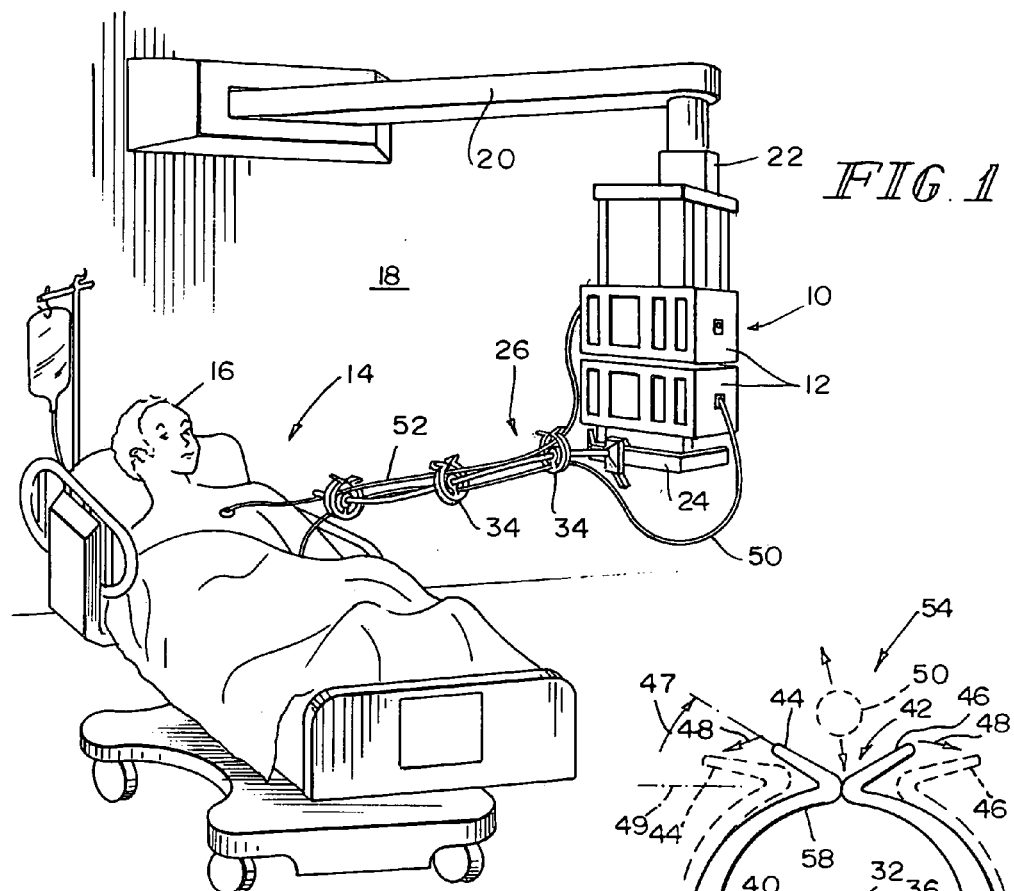
FIG. 1
FIG. 3
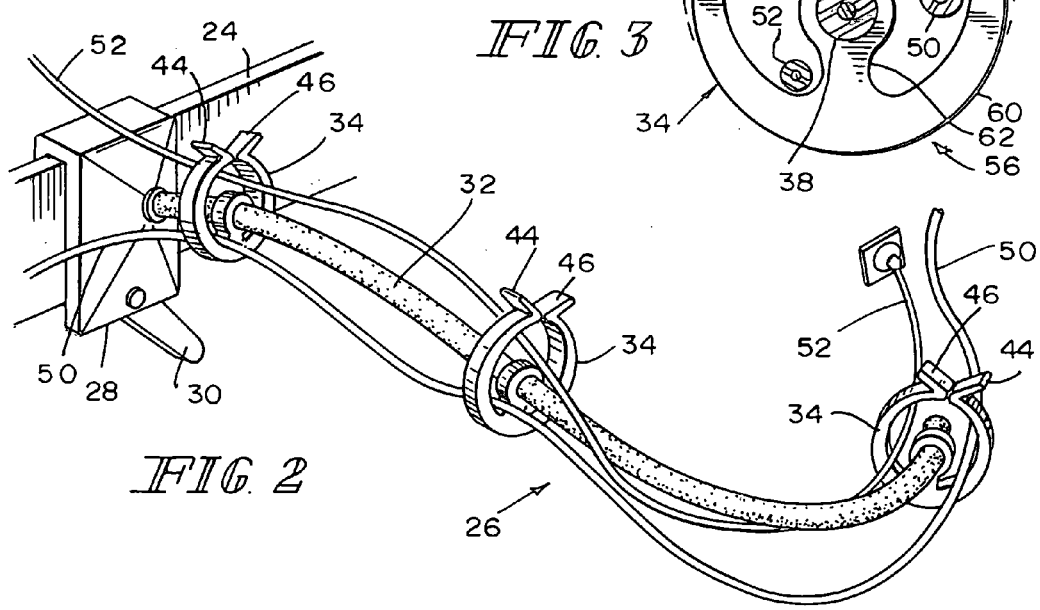
FIG. 2

PATIENT LINE MANAGEMENT SYSTEM

RELATED APPLICATIONS

This application claims priority under 35 U.S.C. 119(e) to U.S. provisional application Ser. No. 60/455,621 filed Mar. 18, 2003, which is expressly incorporated by reference herein.

FIELD OF THE INVENTION

The present disclosure relates to a system for supporting lines such as IV lines, tubes, wires for sensors, etc., and particularly to a system for supporting such lines that extend from patient care equipment toward a patient support.

BACKGROUND OF THE INVENTION

Hospitalized patients often require patient care equipment to be in close proximity during care. Such patient care equipment may include heart monitoring equipment, medical gas delivery equipment, infusion pumps, intra-venous bags, equipment monitors, defibrillators, and other patient care equipment, many of which directly connect to the patient via lines or tubes.

Intravenous lines, tubes, wires and the like have traditionally been left to dangle or hang between patient care equipment and the patient. Sometimes the lines or tubes are secured via a fastener, tape, or other means to a structure for convenient placement in areas that would prevent unintentional movement of the lines or tubes, for example if a caregiver were to trip over or snag one of the lines or tubes. The structure to which the lines or tubes are secured may be a patient support device, a floor, a wall, an equipment support, or any other device that could be used to hold the lines or tubes and resist accidental movement of the lines or tubes.

SUMMARY OF THE INVENTION

The present invention comprises one or more of the following features or elements in the appended claims or combinations thereof. A line management system is provided for supporting patient care lines that extend between a patient and patient care equipment. In this specification and in the appended claims, words such as "extend between a patient and patient care equipment" are intended to define generally where the proximal end and the distal end of the support member are located. The proximal end of the support member may be located generally at, near or adjacent the patient care equipment and the distal end of the support member may be located generally at, near or adjacent the patient or the patient support on which the patient rests. The line management system comprises an elongated support member capable of being manipulated by a caregiver to a selected position where it will stay and hold the position and support the weight of the patient care lines. A line holder is coupled to the support member, the line holder having an opening for insertion of a line to be held. The support member can be mounted on a patient care equipment frame or support.

The support member may comprise a wire and a polymeric coating on the wire. The line holder can be substantially ring-shaped and have a substantially centrally located mount ring for receiving the support member. The support member can be mounted to a bracket and the bracket mounted on the patient care equipment support. The bracket can be movable relative to the patient care equipment support. The bracket can have a lock for locking movement of the bracket relative to the patient care equipment support.

The support member is configured to extend in a cantilevered fashion away from the equipment support and support the weight of a plurality of lines. The support member is configured to be able to be manipulated by a caregiver into a range of positions.

In one embodiment, the line holder comprises a spine having a plurality of arms extending therefrom. The line holder has an open position wherein a line can be inserted and a closed position wherein the line is retained by the line holder. The plurality of arms extend in a substantially parallel direction away from the spine. The line holder may have only two arms.

In the illustrative embodiment, the spine is substantially "C"-shaped, and at least a portion of the spine is flexible so as to allow movement of the arms relative to each other. The line holder may comprise a clasp for selectively holding the line holder in the closed position. The clasp comprises a first tooth on one of the plurality of arms and a second tooth on another of the plurality of arms. The first and second teeth engage each other when the line holder is in the closed position.

A pad can be mounted on one of the plurality of arms, the pad being configured to engage a line without obstructing a flow of a fluid passing through the line.

In this description and in the appended claims, words such as "patient care lines" are intended to cover such lines as IV lines, tubes of various types, wires and sensor wires and the like.

Additional features will become apparent to those skilled in the art upon consideration of the following detailed description of illustrative embodiments exemplifying the best mode of carrying out various systems for transporting and supporting patient care equipment as presently perceived.

BRIEF DESCRIPTION OF THE DRAWINGS

The detailed description particularly refers to the accompanying figures, in which:

FIG. 1 is a perspective view of a flexible line support extending from patient care equipment toward a patient on a bed; the flexible line support carries substantially ring-shaped line holders for holding patient care lines, i.e., fluid and gas lines, in place as they extend between patient care equipment and a patient;

FIG. 2 is a perspective view of the flexible line support of FIG. 1, showing the adjustable mount bracket for mounting the line support on a frame;

FIG. 3 is a cross-sectional view of the flexible line support showing one of the line holders positioned on the line support, the line holder having a closed position and an open position wherein lines can be inserted in the line holder;

DETAILED DESCRIPTION OF THE DRAWINGS

Figure 4:
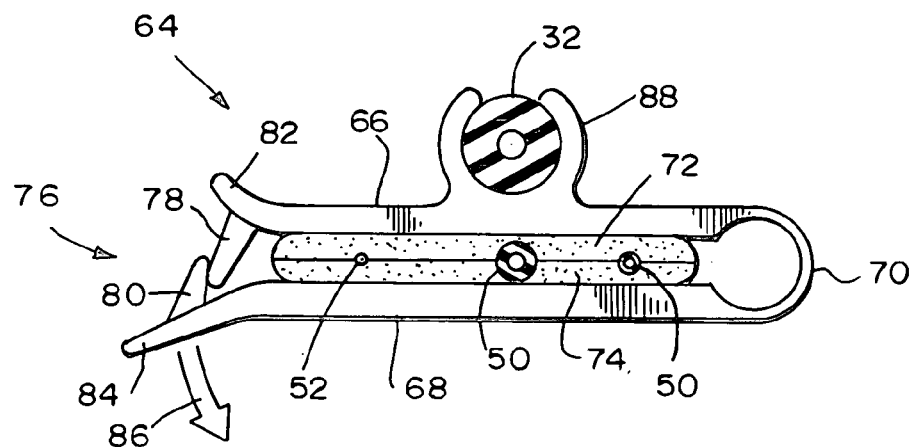
FIG. 4 is an elevation view of an alternate embodiment of a line holder mounted on the flexible line support, the line holder having two elongated arms for holding the patient care lines between the two arms.

A patient care equipment support system 10 is shown in FIG. 1 with patient care equipment 12 mounted thereon. A patient support device 14 is also shown supporting a patient 16 thereon. Patient support device 14 is illustratively a hospital bed, however, it is within the scope of the disclosure to utilize the invention with other patient support devices such as stretchers, chairs, and the like in various types of settings including intensive care rooms, operating rooms, and physician offices.

Patient care equipment support system 10 is illustratively pivotably coupled to a wall 18 via arm 20. A column 22 illustratively depends from a distal end of arm 20, and patient care equipment support system 10 is attached thereto. It should be understood, however, that while the illustrative embodiment comprises an arm 20 having a depending column 22, patient care equipment 12 could be mounted on a wall, a stand, on a patient support device, or on any other structure capable of supporting patient care equipment 12.

As can be seen in FIGS. 1–2, support system 10 illustratively comprises a frame member 24 to which a line support 26 can be attached. Line support 26 is illustratively mounted to frame member 24 via mount bracket 28. Mount bracket 28 illustratively comprises a lever-actuator with a slide lock 30, however, it should be understood that other configurations for a mount bracket 28 are within the scope of the disclosure, and further, that line support 26 can be mounted in any other fashion to frame member 24, including without a mount bracket 28.

Illustratively, as can be seen in FIG. 2, line support 26 comprises an elongated support member 32 that is flexible so that it can be manipulated to extend from bracket 28 in nearly any direction. Illustratively, a plurality of line holders 34 are attached to elongated support member 32 in substantially evenly spaced apart regions.

Elongated support member 32 is illustratively constructed of a malleable wire core 36 having a urethane coating 38 covering wire core 36. The wire core 36 may be bent, formed or shaped to have and hold a desired position established by a caregiver manipulating the member 32. However, it should be understood that such a construction is illustrative and other constructions for support member 32 are within the scope of the disclosure so long as the construction permits support member 32 to be positioned as desired by a caregiver. For example, elongated support member could be a gooseneck of metal or similar material. The gooseneck could have a coating such as rubber. Alternatively, elongated support member could be a sectional support member having ball and socket joints joining together sections of smaller support members.

The support member, therefore, is a member which can be adjusted, bent, formed or otherwise positioned to extend from the equipment support toward the patient and which will hold its position selected by the caregiver. The illustrative support member will extend in a cantilevered fashion and support itself and the weight of the lines.

FIG. 3 shows a cross-sectional view of support member 32 having a wire core 36 and a urethane coating 38 covering wire core 36. In the illustrative embodiment of FIG. 3, line holder 34 is a substantially circular ring having a substantially centrally located mount ring 40 configured to receive elongated support member 32 therein. Additionally, line holder 34 is illustratively formed of a polymeric material having an opening or slot 42 formed in the periphery of line holder 34. Further illustratively, two tabs 44, 46 extend from the periphery of line holder 34 on either side of the slot 42. The polymeric material of line holder 34 illustratively holds tabs 44, 46 adjacent each other unless tabs 44, 46 are caused to be spread apart from each other when a tube or line is pushed through slot 42.

As used herein, the words "tube", "line", and "patient care line" refer generally to any conduit or electrical wire that could be used in a medical setting or a patient care environment including, but not limited to, IV tubes, sensor wires, oxygen-, gas-, or fluid-carrying tubes and the like. Furthermore, the words "tube," "line," and "patient care line" may be used interchangeably and still refer generally to the definitions described above.

As can be seen in FIG. 3, tabs 44, 46 are illustratively ramped at an acute angle 47 relative to a tangential line 49 drawn across line holder 34 at slot 42. Such an acute angle 47 facilitates the movement of tabs 44, 46 apart from each other in the direction shown by arrows 48 such that a gap is formed between tabs 44, 46, as shown in phantom in FIG. 3. Tabs 44, 46 spread apart when a tube 50 or line 52 is inserted through slot 42, as can be seen in phantom in FIG. 3. In the alternative, tabs 44, 46 may be spread apart by a caregiver's fingers.

Illustratively, line holder 34 is configured to have a slotted end 54, visible in FIG. 3 and a mount end 56. Walls 58 of slotted end 54 are illustratively of smaller thickness than walls 60 of mount end 56. The thicker walls 60 provide additional structure and durability for repeated use of line holder 34, particularly repeated movement of tabs 44, 46 relative to each other.

Illustratively, a neck 62 extends from mount end 56 radially inwardly toward a central portion of line holder 34. Mount ring 40 is formed at the distal end of neck 62, mount ring 40 being configured to engage elongated support member 32. Illustratively, mount ring 40 of line holder 34 is sized such that a friction fit is formed between elongated support member 32 and mount ring 40, thereby permitting line holder 34 to move relative to elongated support member 32 under the urging of a caregiver. However, line holder 34 is stationary relative to elongated support member 32 at any other time. It should be understood that mount ring 40 could be of various other constructions, such as a "C"-shaped mount, as can be seen in FIGS. 4–5.

Figure 5:
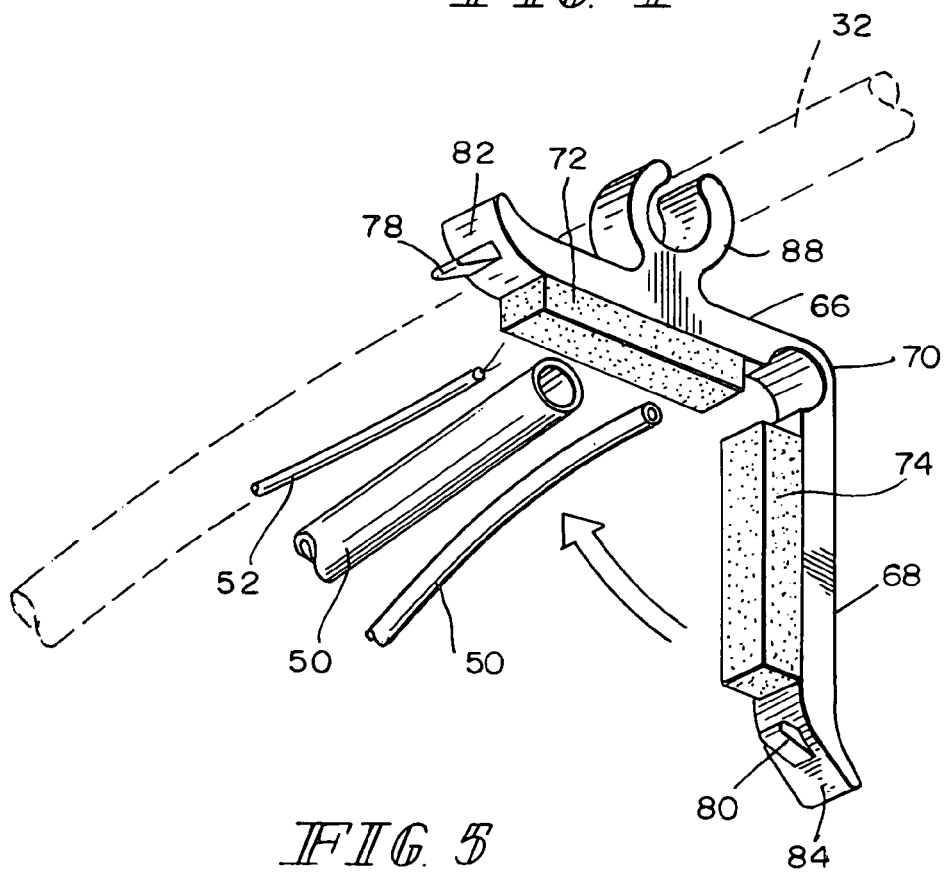
FIG. 5 is a perspective view of the line holder of FIG. 4, showing the elongated arms hinged open so as to accept patient care lines therebetween.

In another embodiment, shown in FIGS. 4–5, a line holder 64 is formed such that two arms 66, 68 extend from a central spine 70 that is illustratively flexible in order to allow arms 66, 68 to move relative to each other as spine 70 is flexed. Illustratively, each arm 66, 68 has a pad 72, 74 attached (respectively) to the arm. Pads 72, 74 are illustratively foam pads that cooperate to position tubes 50 and lines 52 between the pads when arms 66, 68 are moved into a parallel position relative to each other, as shown in FIG. 4. However, although the illustrative embodiment uses pads 72, 74 to hold tubes 50 and lines 52 in place, it is within the scope of the disclosure to utilize other materials and constructions that would hold tubes 50 and lines 52 in place, or to use only one pad or no pads. For example, line holder 64 could be a solid-piece material (i.e., rubber) that is resilient and can flex about spine 70, yet hold lines 52 and tubes 50 in place when in the closed position. Line holder 64 may alternatively be constructed so as to permit movement of lines 52 and tubes 50 when in the closed position.

Illustratively, line holder 64 further includes a clasp 76 comprising a first tooth 78 and a second tooth 80 that engage each other in the closed position shown in FIG. 4, thereby holding clasp 76 in the closed position until clasp 76 is released by a caregiver by pulling on one of ramped ends 82, 84 of arms 66, 68. Illustratively, ramped end 82 supports tooth 78 that extends outwardly therefrom, and ramped end 84 supports tooth 80 that extends outwardly therefrom. Illustratively, when a caregiver pulls ramped end 84 in the direction indicated by arrow 86, ramped end 84 flexes and causes tooth 80 to move out of engagement with tooth 78, at which time clasp 76 can be opened. However, it should be understood that other clasps and methods of holding arms 66, 68 substantially parallel are within the scope of the disclosure.

Line holder 64 illustratively comprises a mount that fittingly engages an elongated support member 32, as can be seen in FIGS. 4–5. Mount 88 is illustratively "C"-shaped, however, other configurations are within the scope of the disclosure. Mount 88 is configured to engage support member 32 such that it can be moved relative to support member 32 when urged by a caregiver, but it otherwise maintains its position on support member 32 during use.

It is conceivable and within the scope of the disclosure for line holder 64 to have more than two arms. Such a construction could allow for lines and tubes to be held in a plurality of locations in the line holder.

Although the invention has been described in detail with reference to certain illustrative embodiments, variations and modifications exist with the scope and spirit of this disclosure as described and defined in the following claims.

The invention claimed is:

1. A line management system for supporting patient care lines that extend between a patient and patient care equipment, the system comprising
    an elongated support member that is adjustable to a plurality of self-supporting positions, and
    a line holder coupled to the support member, the line holder having a radially-extending opening for insertion of a line to be held, the line holder having flexible portions that extend outwardly from a periphery of the line holder on the opposite sides of the radially-extending opening through which the line to be held is inserted, the flexible portions being configured to be engaged by the line to be held during insertion thereof through the radially-extending opening, the line holder comprising a mount ring surrounding the elongated support member, the mount ring being free of any slots extending radially therethrough.

2. The system of claim 1, wherein the support member comprises a wire and a polymeric coating on the wire.

3. The system of claim 1, wherein the support member is mounted on a patient care equipment support.

4. The system of claim 3, wherein the support member is mounted to a bracket and the bracket is mounted on the patient care equipment support.

5. The system of claim 4, wherein the bracket is movable relative to the patient care equipment support.

6. The system of claim 5, wherein the bracket has a lock for locking movement of the bracket relative to the patient care equipment support.

7. The system of claim 3, wherein the support member is configured to extend in a cantilevered fashion away from the equipment support to support the weight of a plurality of lines.

8. The system of claim 1, wherein the support member is able to be manipulated by a caregiver into a range of positions.

9. The system of claim 1, wherein the line holder is made from polymeric material.

10. The system of claim 1, wherein the line holder further comprises a generally circular outer ring having the mount ring located generally centrally thereof.

11. The system of claim 10, wherein the mount ring defines an axially extending bore through which the elongated support member is routed.

12. The system of claim 11, wherein the axially extending bore in the mount ring is sized such that a friction fit is formed between the elongated support member and the mount ring.

13. The system of claim 10, wherein the radially-extending opening is formed in the outer ring.

14. The system of claim 13, wherein the flexible portions extend outwardly from the opposite sides of the radially-extending opening in the outer ring.

15. The system of claim 14, wherein the flexible portions are normally disposed adjacent each other and the flexible portions are caused to spread apart from each other when a line to be held is pushed through the radially-extending opening in the outer ring.

16. The system of claim 14, wherein the flexible portions are ramped at an acute angle relative to a tangential line extending through the radially-extending opening.

17. The system of claim 10, wherein the outer ring of the line holder has a slotted end and a mount end, and walls of the outer ring near the mount end are thicker than walls of the outer ring near the slotted end.

18. The system of claim 10, wherein the line holder further comprises a neck portion that extends radially inwardly from the outer ring to the mount ring.

19. A line management system for use with a support structure and for supporting patient care lines, the system comprising
    an elongated support member having a proximal end and a distal end, the support member being manipulatable into a plurality of self-supporting positions by a caregiver and configured to hold such positions such that its distal end is supported in space when its proximal end is supported by the support structure, the elongated support member comprising a malleable wire, the wire being free from any axial opening therethrough, and
    a line holder coupled to the support member, the line holder having a radially-extending opening for insertion of a line to be held.

20. The system of claim 19, wherein the wire has a polymeric coating thereon.

21. The system of claim 20, wherein the polymeric coating on the wire comprises urethane coating.

* * * * *